(12) United States Patent
Chappel et al.

(10) Patent No.: US 11,433,180 B2
(45) Date of Patent: *Sep. 6, 2022

(54) VENTED RESERVOIR FOR MEDICAL PUMP (71) Applicant: DEBIOTECH S.A., Lausanne (CH)

(72) Inventors: Eric Chappel, Versonnex (FR);
Ricardo Allendes, Lausanne (CH);
Frédéric Neftel, Lausanne (CH)

(73) Assignee: DEBIOTECH S.A., Lausanne (CH)

( * ) Notice: Subject to any disclaimer, the term of this patent is extended or adjusted under 35 U.S.C. 154(b) by 339 days.

This patent is subject to a terminal disclaimer.

(21) Appl. No.: 16/673,280

(22) Filed: Nov. 4, 2019

(65) Prior Publication Data
US 2020/0061287 A1    Feb. 27, 2020

Related U.S. Application Data (63) Continuation of application No. 15/876,006, filed on Jan. 19, 2018, now Pat. No. 10,471,203, which is a
(Continued)

(30) Foreign Application Priority Data

Jun. 23, 2011 (EP) ........................... 11171155
Jul. 4, 2011 (EP) ........................... 11172494

(51) Int. Cl.
*A61M 37/00* (2006.01)
*A61M 5/142* (2006.01)
(Continued)

(52) U.S. Cl.
CPC .... *A61M 5/14244* (2013.01); *A61M 5/14593* (2013.01); *A61M 5/16859* (2013.01);
(Continued)

(58) Field of Classification Search
CPC .......... A61M 5/14244; A61M 5/14593; A61M 5/16859; A61M 5/16881; A61M 5/142;
(Continued)

(56) References Cited

U.S. PATENT DOCUMENTS 5,047,790 A   9/1991 Cowger et al.
5,759,014 A   6/1998 Van Lintel
(Continued)

FOREIGN PATENT DOCUMENTS

CA    2647355 A1   10/2007
CA    2741195 A1    4/2010
(Continued)

OTHER PUBLICATIONS

Bourouina, Tarik, et al., "Modeling micropumps with electrical equivalent networks," Journal of Micromechanics and Microengineering, vol. 6, 1996, pp. 398-404.
(Continued)

Primary Examiner — Rebecca E Eisenberg
(74) Attorney, Agent, or Firm — Nixon & Vanderhye P.C.

(57) ABSTRACT

The present invention concerns a medical pump comprising: a. A hard housing comprising a top (24) and bottom (1) hard shells, within which a rigid wall (3) and a movable membrane (2) create three distinct chambers; wherein i. said movable membrane tightly separates said second (29) and third (22) chambers ii. said first and third chambers have a watertight interface iii. said second chamber (29) is designed to contain a fluid iv. said first chamber (23) comprises a first venting mean (20) which is arranged to provide a fluidic communication between said first chamber (23) and the external environment; v. said third chamber (22) comprises a second venting mean which is arranged to provide a fluidic communication between said third chamber (22) and the external environment b. A pumping element (4) located in
(Continued)

the first chamber (23) c. A least one pressure sensor which measure the pressure gradient between the first chamber (23) and the second chamber (29) d. A fluid pathway which permits: i. a first fluid connection (27) between said second chamber (29) and said pumping element ii. a second fluid connection (28) between said pumping element and a patient line (30).

38 Claims, 4 Drawing Sheets

Related U.S. Application Data continuation of application No. 15/062,086, filed on Mar. 5, 2016, now Pat. No. 9,872,955, which is a continuation of application No. 14/128,959, filed as application No. PCT/IB2017/053177 on Jun. 22, 2012, now Pat. No. 9,284,960.

(51) Int. Cl.
*A61M 5/168* (2006.01)
*A61M 5/145* (2006.01)
*A61M 5/50* (2006.01)
*F04D 15/00* (2006.01)

(52) U.S. Cl.
CPC ...... *A61M 5/16881* (2013.01); *A61M 5/5086* (2013.01); *F04D 15/0005* (2013.01)

(58) Field of Classification Search
CPC .......... A61M 5/14224; A61M 5/16831; A61M 5/16854
See application file for complete search history.

(56) References Cited

U.S. PATENT DOCUMENTS

| 7,104,763 | B2 | 9/2006 | Bouton et al. |
| 2004/0133166 | A1 | 7/2004 | Moberg et al. |
| 2008/0011550 | A1 | 1/2008 | Dunn et al. |
| 2008/0214979 | A1 | 9/2008 | Brugger et al. |
| 2009/0145236 | A1 | 6/2009 | Esnouf |
| 2011/0054397 | A1* | 3/2011 | Menot .............. A61M 5/16854 604/110 |
| 2011/0142688 | A1 | 6/2011 | Chappel et al. |

FOREIGN PATENT DOCUMENTS

| EP | 1762263 | A1 | 3/2007 |
| EP | 2537545 | A1 | 12/2012 |
| EP | 2543404 | A1 | 1/2013 |
| JP | H04250062 | A | 9/1992 |
| JP | 2006136469 | A | 6/2006 |
| JP | 2008019857 | A | 1/2008 |
| JP | 2009531111 | A | 9/2009 |
| JP | 2010260597 | A | 11/2010 |
| WO | 2007113708 | A1 | 10/2007 |
| WO | 2010046728 | A1 | 4/2010 |

OTHER PUBLICATIONS

Dumont-Fillon, Dimitry, et al., "Insulin Micropump with Embedded Pressure Sensors for Failure Detection and Delivery of Accurate Monitoring," Micromachines, vol. 5, No. 4, 2014, pp. 1161-1172.
Schneeberger, N., et al., "Drug Delivery Micropump with Built-In Monitoring," Procedia Chemistry, vol. 1, No. 1, 2009, pp. 1339-1342.
Communication pursuant to article 94(3) EPC dated Jul. 24, 2020, issued in European Application No. 12740216.2, 8 pages.
English translation of Notice of Reasons for Rejection dated Mar. 22, 2016, issued in Japan Patent Application No. 2014-514686, 7 pages.
Office Action dated Apr. 24, 2018, issued in Canada Patent Application No. 2,835,174, 7 pages.
English translation of Notification of Reasons for Refusal dated Jun. 19, 2018, issued in Japan Patent Application No. 2017-138937, 7 pages.
U.S. Appl. No. 16/409,344, filed May 10, 2019.

* cited by examiner

VENTED RESERVOIR FOR MEDICAL PUMP

CROSS-REFERENCE TO RELATED APPLICATIONS

This application is a continuation application of U.S. application Ser. No. 15/876,006, that was filed on Jan. 19, 2018, now U.S. Pat. No. 10,471,203 which in turn is a continuation application of U.S. application Ser. No. 15/062,086, that was filed on Mar. 5, 2016, now U.S. Pat. No. 9,872,955, which in turn is a continuation application of U.S. application Ser. No. 14/128,959 that was filed on Dec. 23, 2013, now U.S. Pat. No. 9,284,960, which in turn is the U.S. national phase of International Application No. PCT/IB2012/053176, filed 22 Jun. 2012, which designated the U.S. and claims foreign priority to EP Application No. 11171155.2, filed Jun. 23, 2011, and EP Application No. 11172494.4, filed Jul. 4, 2011, the entire contents of each of which are herewith incorporated by reference.

FIELD OF INVENTION

The present invention is related to medical pumps, more specifically to reservoirs used with insulin pumps and means to prevent and detect any over or under pressure in the reservoir.

STATE OF THE ART

Figure 1:
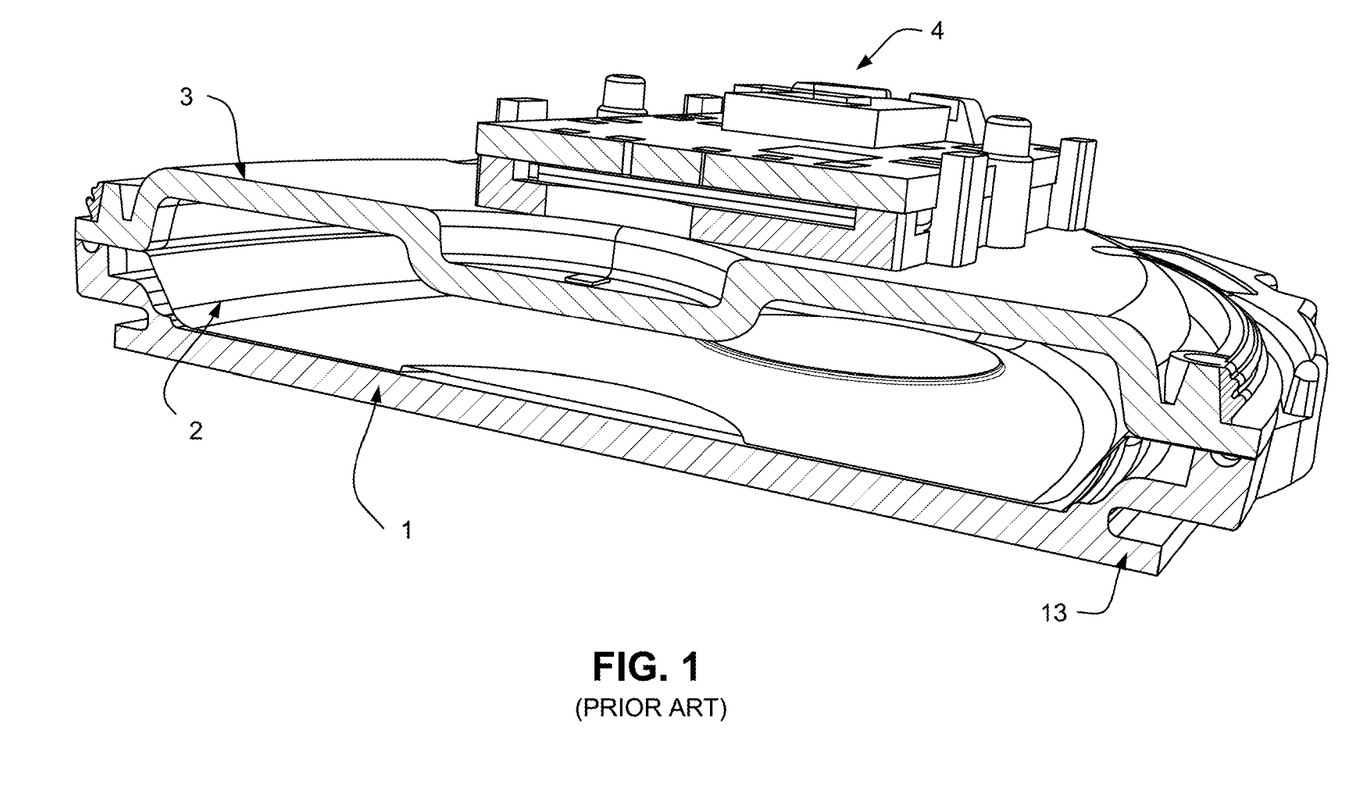
FIG. 1 shows the prior art of the medical device without the holes.

Some insulin pumps, such as the one illustrated on FIG. 1, have a rigid chamber defined between a rigid wall (3) and bottom (1) hard shell. A pumping element (4) is fixed to the rigid wall (3). The chamber contains a reservoir which is made of a movable membrane (2) (e.g. soft pouch or flexible film), such as thermoformed and heat-soldered onto the rigid wall (3) (see for instance international patent application WO 2007/113708). The bottom hard shell (1) protects the membrane (2) against external mechanical forces and ensures a water tightness of the system. The pump is vented using a hydrophobic filter in order to prevent a pressurization of the reservoir due to pressure or temperature changes. The risk of clogging with this filter is high and therefore a potential overdose becomes possible. Moreover such clogging cannot be detected with the gauge pressure detector of the pump because the reference port of the detector is vented by the same filter than the reservoir itself. Therefore, said device described by WO 2007/113708 can't detect a possible clogging of this vent which cause an over or under delivery of the insulin to the patient.

The implementation of an additional anti-free-flow valve is a possible way to overcome this problem. See WO 2008/029051. However, this may be expensive for a disposable product and may not be totally fail safe.

GENERAL DESCRIPTION OF THE INVENTION

The present invention provides another advantageous solutions to prevent an over or under delivery of fluid to the patient (for example: insulin) which is induced when the pressure gradient between the reservoir and the external environment changes. Furthermore, the present invention may advantageously use with a method described in the application EP 11172494.4.

To this effect, it relates to a medical pump comprising three distinct chambers. Said medical device is designed to form a hard housing comprising a top and bottom hard shells. Said housing further comprises a hard wall and a movable membrane which create said three distinct chambers. Said movable membrane tightly separates the second and the third chambers. The first and third chambers have a watertight interface. Said second chamber is designed to contain a fluid. Said movable membrane may be moved between said rigid wall and the bottom hard shell, in such a way that the fluid tight reservoir is formed by the second chamber. Said first chamber comprises a first venting mean which is arranged to provide a fluidic communication between said first chamber and the external environment. Said third chamber comprises a second venting mean which is arranged to provide a fluidic communication between said third chamber and the external environment. The device further comprises a pumping element located in the first chamber, at least one pressure sensor which measures the pressure gradient between the first chamber and the third chamber. Said medical device comprises a fluid pathway which permits a first fluid connection between said second chamber and said pumping element and a second fluid connection between said pumping element and a patient line.

With the present invention, the third chamber is completely vented by said second venting mean while maintaining the protection against mechanical forces or ingress of solid foreign objects such as sharp tips. In one of embodiment, said second venting mean is formed by several passages. The protection against water ingress is not insured for the third chamber, which is not necessary if said movable member is a tight membrane. While, the first chamber is vented by a vent which may be hydrophobic and or oleophobic to protect the electronic part.

In one of embodiment, said movable membrane may transmit the pressure of the third chamber to said first fluid connection via the second chamber and the movable membrane. If, one or the both venting means get clogged, the pressure in the device and the pressure of the external environment may be different. The pressure gradient between inside device, in particular in the third chamber, and the external environment may induce an over or under delivery of the fluid to the patient.

For this reason, the second venting mean comprises several passages (which reduce the clogging risk) and the device uses a method partially described in the application EP 11172494.4 for detecting if at least one venting means is clogged.

The sensors may be localised in said chambers, in said fluid connections and/or outside.

The sensor may be a gauge pressure sensor localised between:
 the third chamber and the first chamber, and/or
 said first fluid connection and the first chamber, and/or
 said second fluid connection and the first chamber, and/or
 said third chamber and external environment, and/or
 said first chamber and external environment.

The reference port of said gauge pressure sensors may be the external environment, the first chamber or the third chamber.

In one of embodiment, the device comprises processing means for the sensor signal which may measure the pressure gradient between the third chamber and the first chamber or the external environment. And said processing means detect a under or over pressure in said first chamber and/or said third chamber.

Said processing means can detect the clogging of said first venting mean and/or said second venting mean.

The medical pump comprises alarm means which alert the patient in case of said first venting mean and/or said second venting mean are clogged.

LIST OF ELEMENTS

1 Bottom hard shell
2 Movable membrane
3 Rigid wall
4 Pumping element
5 Holes
6 Baffles
7 Second venting mean
8 Upper face of the second chamber and/or third chamber
9 Lower face of the third chamber
10 Lateral face of the third chamber
11 Marks on the bottom shell
12 Filling port of the second chamber
13 Lateral slides
14 Grips
16 Battery
17 PCB (Printed Circuit Board)
18 Spring contacts
19 Battery contact
20 First venting mean
21 Lock
22 Third chamber
23 First chamber
24 Top hard shell
25 Upper face of the first chamber
26 Lower face of the first chamber
27 First fluid connection
28 Second fluid connection
29 Second chamber
30 Patient line

DETAILED DESCRIPTION OF THE INVENTION

The medical pump of the present invention comprises three distinct chambers (23, 29, 22). The second chamber (29) and the third chamber (22) is separated by a movable membrane (2) which may be moved between a bottom hard shell (1) and the rigid wall (3) and comprises an upper face (8), a lower face (9) and a lateral face (10). Said bottom shell (1) contains several holes (5) which are forming the internal ends of passages (7) communicating between the third chamber and the external environment.

The first chamber (23) is defined between the top hard shell (24) and the rigid wall (3). Said first chamber (23) comprises an upper face (25), a lower face (26), a pumping element (4) and a first venting mean (20).

The third chamber and the first chamber are tightly separated by at least said rigid wall (3) which is designed to form a watertight interface.

In one of said embodiments, a hydrophobic surface treatment or coating can also be used on and/or around the holes (5) to limit the water ingress.

In one of said embodiments, said first chamber (23) comprises the electronic elements.

In one of said embodiments, the lateral faces of said chambers are formed by the junction between part of the top and the bottom hard shell of the medical device.

The medical device comprises a first fluid connection (27) between said second chamber (29) and said pumping element, and a second fluid connection (28) between said pumping element and the patient line.

A sensor may measure a pressure gradient between the fluid and said first chamber (23) and/or said third chamber (22) or between said both chambers. Said sensor can be located upstream and/or downstream of the pumping element (4).

In a preferred embodiment, the sensor is a gauge pressure sensor. The reference port of said gauge pressure sensor is connected to said first chamber (23), allowing the detection of under or over pressure between:
    said third and first chambers, and/or
    the fluid and said first chamber, and/or
    the fluid and said third chamber, and/or
    the fluid and the patient line.

In case of one or both of said venting means are clogged, a positive or negative pressure may be trapped in the third chamber (22) and/or in the first chamber (23). Therefore, the device further comprises alarm means which can alert the patient if the first venting mean (20) of the first chamber or/and the second venting mean (7) of said third chamber (22) are clogged.

Vent Clogging Case Studies:

In a preferred embodiment, the change of pressure due to clogging can be monitored using two gauge sensors located in the pumping element. A first gauge pressure sensor is located in the first fluid connection (27) which may measure the pressure of the third chamber which is transmitted to the second chamber (29) (and the first fluid connection (27)) via the movable membrane (2). A second gauge pressure sensor is located in the second fluid connection (28) which may measure the pressure of the patient line. For both sensors, the reference port is the first chamber (23).

1. Clogging of the second venting mean (7) only→potential over or under pressure in the third chamber (22) is transmitted to the fluid in the second chamber (29) via the membrane (2) and is detected via the first sensor since the reference port (the first chamber (23)) of said sensor is not pressurized. The first sensor detects a pressure gradient between the third chamber (22) and the first chamber (23) while the second sensor doesn't detect any pressure gradient between the patient line and the first chamber (23).

2. Clogging of the first venting mean (20) only→the first chamber (23) and therefore the reference ports of both sensors shall potentially exhibit over or under pressure with respect to external environment. Said over or under pressure will be detected by both sensors. Positive (respectively negative) pressure in said first chamber (23) leads to a pressure signal equivalent to a negative (resp. positive) pressure in the pumping chamber in normal conditions. Therefore, a clogging of said first venting mean (20) is detected when the pressure in the first chamber (23)

becomes different from external environment pressure. Said difference of pressure inducing the same offset on both gauge pressure sensors with respect to a reference value obtained either by measuring the pressure sensor signal before the priming of the pump or by using calibration data.

3. Clogging of all venting ports→the first and third chambers (23, 22) are potentially in over or under pressure with respect to the external environment. Therefore, the first sensor can't detect any pressure gradient between the first and the second or third chambers. But, the patient line pressure may be different. Therefore, the second sensor can detect a pressure gradient between the first chamber (23) and the patient line.

Figure 2:
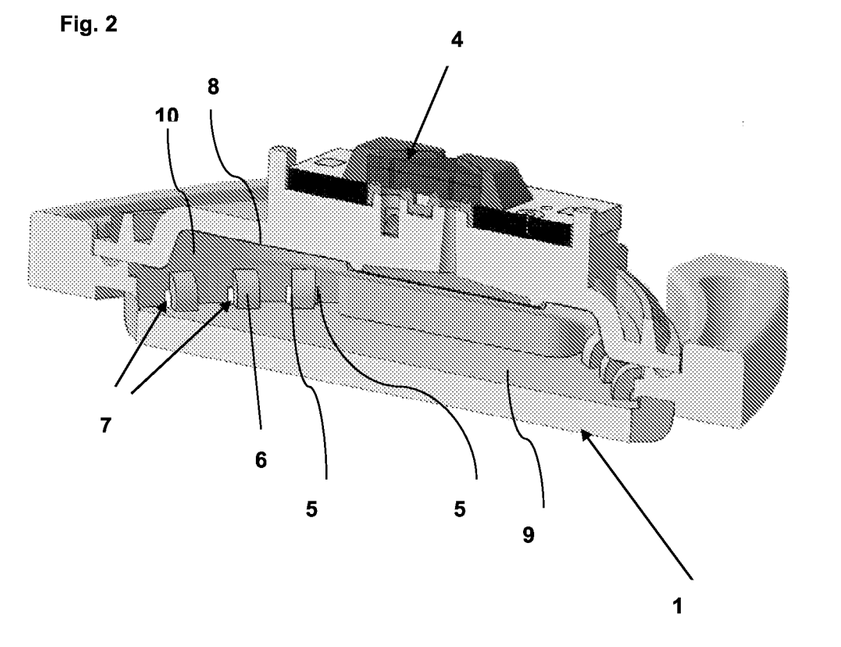
FIG. 2 illustrates an embodiment of the invention with several holes on one of hard shells
Figure 3:
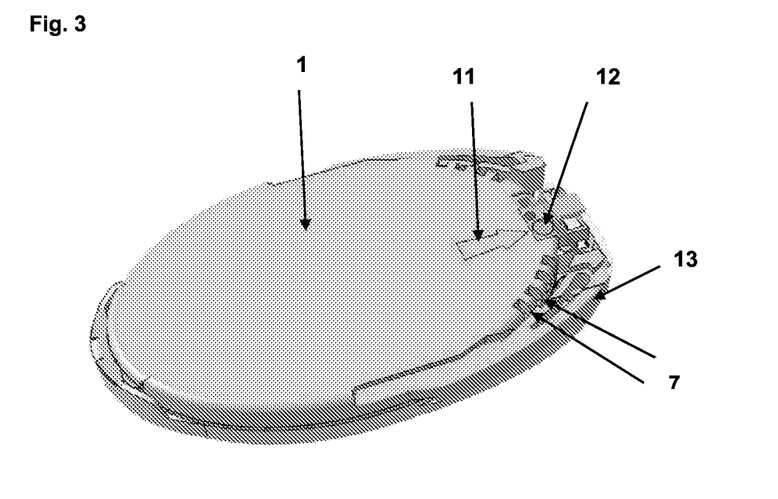
FIG. 3 represents the same embodiment as the one illustrated on FIG. 2 but viewed from the other side.

FIG. 2 illustrates an embodiment of the invention where the bottom shell (1) is provided with passages (7) on its lateral face (10) of the third chamber. Each passage (7) is provided with a baffle (6) which defines two opposite holes (5) oriented towards said lateral face (10), in a direction which is parallel with respect to the bottom face. In another embodiment, the holes are located within said lateral face (10) or said lower face (9) of the third chamber.

In a preferred embodiment, said holes (5) are oriented in a direction which is forming an angle above 30° with the main direction of their respective passages (7).

Figure 4:
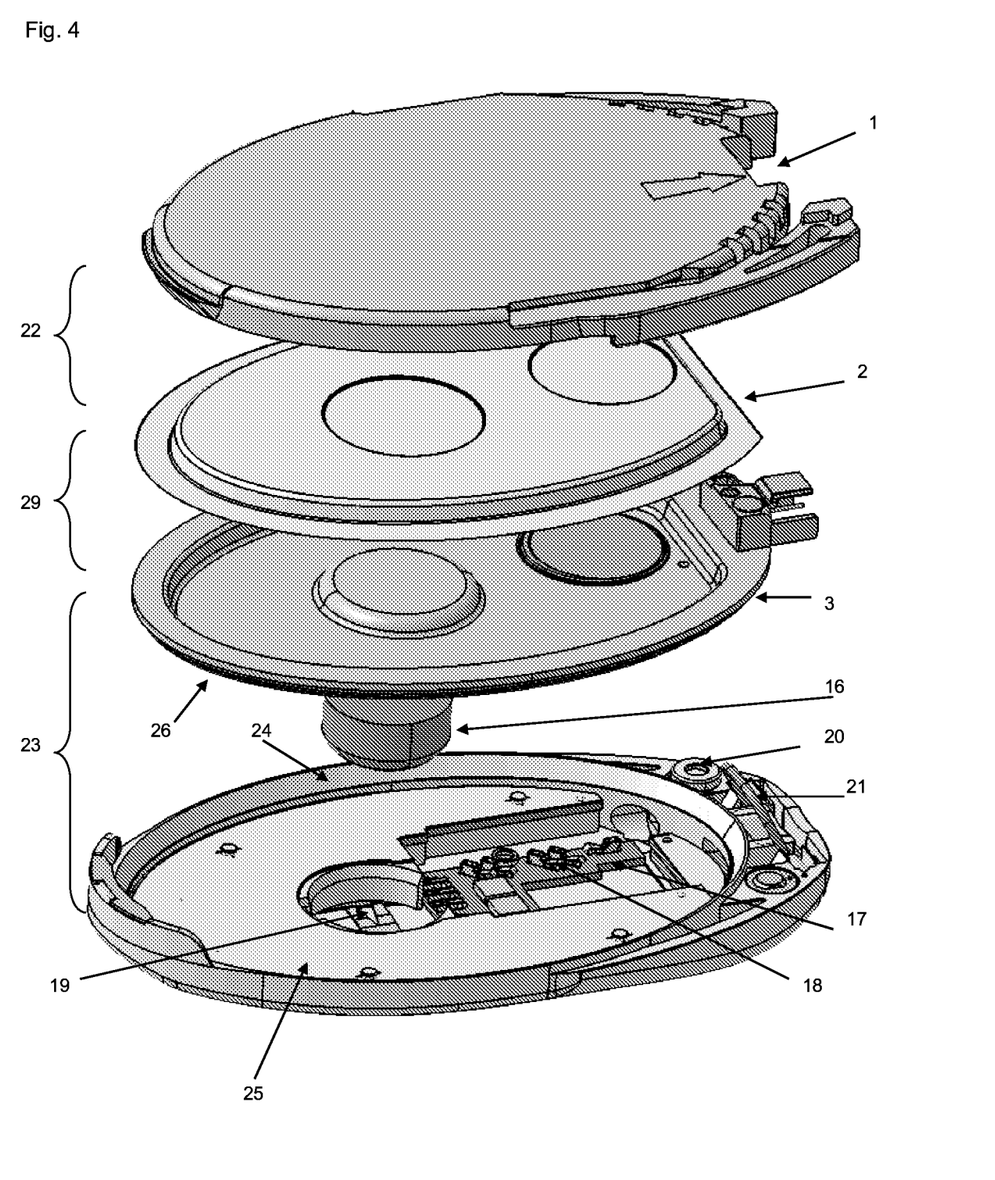
FIG. 4 shows an exploded view of the complete system.
Figure 5:
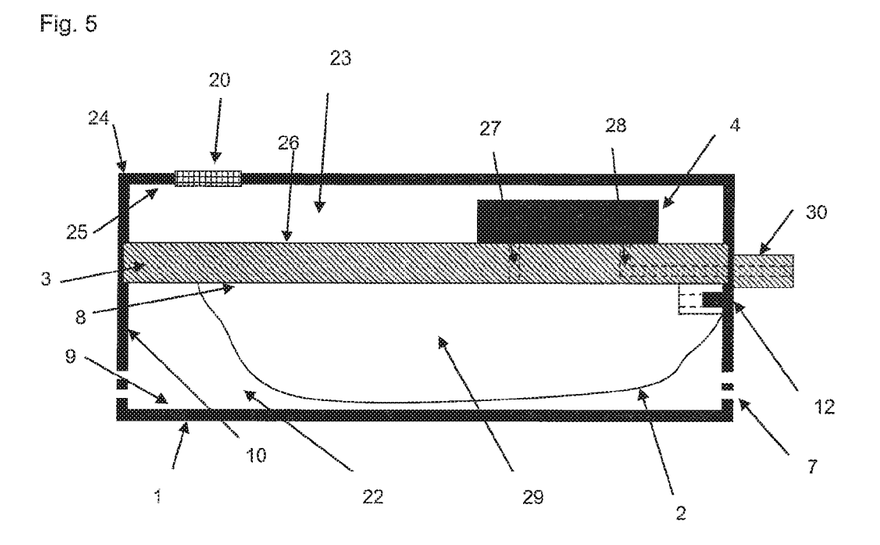
FIG. 5 shows the embodiment of the medical device with both venting means are directly connected to the external environment.

FIG. 4 shows an exploded view of the complete system, including the same embodiment as to the one illustrated on FIG. 2 and the top hard shell (24), the battery (16), a lock (21), the first venting mean (20), a PCB (17) and its spring contacts (18) to connect the pumping element (4) (not showed here) and finally the battery contact (19).

In the present invention the design of the bottom shell and more particularly the second venting mean (7) are driven by:
The capability to vent the membrane (2) for any foreseeable use or probable misuse of the pump, including the presence of dirt onto the pump, the wearing of the pump under clothes . . .
The protection against solid foreign objects When second venting means (7), which is several passages like holes (5), are provided in the bottom shell (1) it is not possible to accidentally close all openings because of their specific locations. The compression of the pump against a soft material on the top shell cannot typically obstruct these passages because of their lateral orientated location. The closure of the passages by lateral compression is also prevented by baffles (6) that limit the access typically to fingers.

The passages (7) may have the shape of a slit or any other shape having one dimension preferably lower than 1 mm.

The passages (7) may also be made into a recess and oriented perpendicularly to the normal of the lateral face (10) of the third chamber (22) in order to prevent the insertion of a straight and rigid tip, the minimum dimension of the opening being preferably no longer limited to 1 mm in this configuration according to this recess.

The bottom shell (1) is preferably transparent; the patient should be able to see any large obstruction due to foods or any sticky stuff and eventually to change the disposable.

The bottom shell (1) and/or the rigid wall (3) and/or the membrane (2) are preferably made in plastic, and more generally in any material having specific grades compatible with insulin. The use of the same material is desirable for thermowelding. The contact surfaces for gluing or thermowelding between the top and bottom shell should be large enough to withstand reservoir overpressure up to 1 bar and drop test from a height of 1 meter or more.

The membrane material has ideally a low elasticity and a low permeability. The membrane thickness is typically smaller than 100 microns.

The surface of the membrane (2) is ideally larger than the surface of the lower face (9) of the third chamber (22) of the bottom shell to prevent any in-plane stress in the membrane and therefore any effect due to the membrane elasticity.

The bottom shell (1) can advantageously include Moiré pattern. In case of overfilling of the reservoir, when the membrane is directly in contact with the bottom shell, the reservoir pressure would bend the bottom shell and induce changes in the Moiré pattern, giving a visual feedback of overfilling to the patient. The Moiré pattern covers partly the bottom shell (1) surface in order to make possible the observation of bubbles into the reservoir.

The bottom shell may include any means to detect deformation due to static load or a pressurized reservoir (e.g. strain gauges, pressure sensors . . . ).

The passages (7) may be partly or completely covered by a removable and permeable tape that ensures the venting of the reservoir. In case of projection of sticky stuff on the passages (7) the patient can advantageously remove the tape instead of trying to clean up the device or simply changing it. The tape may be made of several sheets that can be removed iteratively. Such air permeable tape may also cover the first venting mean (20) of the first chamber (23).

The bottom shell (1) may include marks (11) that help the patient to find the filling port (12) containing a septum.

The bottom shell (1) is ideally flat and has lateral slides (13) for patch insertion (clipping) and grips (14) for patch removal (unclipping).

Fluid, e.g. water, can flow through the passages (7) and then in the space between the bottom shell (1) and the membrane (2), the fluid tightness being only provided to the first chamber (23) of the pump which, among other elements, includes the battery (16). The electronic and pump controller are in the first chamber which is water tight but has to be vented in case a zinc-air battery needing oxygen and when a gauge pressure sensors are used. The first chamber (23) is tightly assembled using lock (21) or clips or any other means onto the upper face of the rigid wall (3), contacting electrically the pads of the pump via the spring contacts (18) of the Printed Circuit Board (PCB) (17).

The first chamber (23) uses the first venting mean (20) which is therefore preferably hydrophobic and/or oleophobic.

Figure 6:
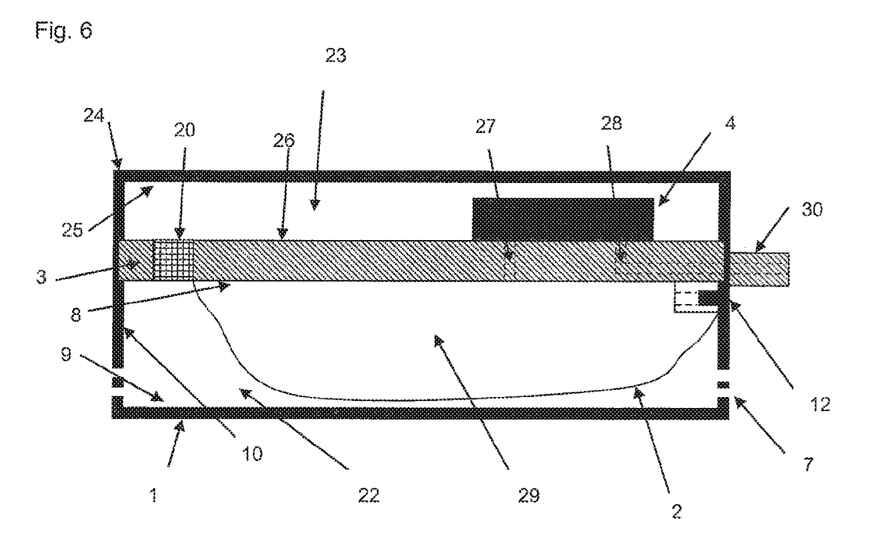
FIG. 6 shows another embodiment of the medical device with the first venting mean located between the first and the third chambers.

In another embodiment (FIG. 6), the first venting mean (20), which is hydrophobic, is located between the first and the third chambers.

In another embodiment, the device further comprises three distinct venting means. The first venting mean connects directly the first chamber to the external environment, the second venting mean connects directly the third chamber to the external environment and the third venting mean is located between the third and the first chamber. This embodiment insure a good venting in third and first chambers even if one venting mean is clogged. Said third venting mean is preferably hydrophobic and/or oleophobic.

The invention claimed is:
1. A delivery medical device comprising:
a hard housing having a bottom hard shell and a top hard shell, the hard shell housing including a first chamber, a second chamber intended to store a fluid to be delivered to a patient, and a third chamber separated by at least a movable membrane and a rigid wall, wherein the second chamber and the third chamber are tightly separated by the movable membrane and the first chamber and the third chamber have a watertight interface;

a fluid pathway configured to provide a fluid communication between the second chamber and the patient;

a pumping device configured to convey the fluid through the fluid pathway to the patient;

a vent device configured to vent at least one of the first chamber and the third chamber to the external environment of the delivery medical device; and an energy source for the pumping device located in the first chamber.

2. The device according to claim 1, wherein the energy source requires communication with ambient air.

3. The device according to claim 1, wherein the vent device is configured to vent at least one of the first chamber and the third chamber to provide a fluidic communication or a pressure equilibration between the first chamber and the air ambient or between the third chamber and the air ambient.

4. The device according to claim 1, wherein the vent device includes a first vent configured to vent the first chamber to the external environment of the delivery medical device.

5. The device according to claim 4, wherein the first vent includes a hydrophobic vent.

6. The device according to claim 1, wherein the vent device includes a second vent configured to vent the third chamber to the external environment of the delivery medical device.

7. The device according to claim 6, wherein the second vent provides an air communication and a liquid communication between the external environment and the third chamber.

8. The device according to claim 1, wherein the vent device includes a passage which extends toward inside the delivery medical device up to a baffle.

9. The device according to claim 8, wherein the baffle includes two opposite holes.

10. The device according to claim 8, wherein the baffle provides a mechanical protection against a tip object from the external environment.

11. The device according to claim 1 further comprising: a pressure transducer requiring a pressure equilibration with ambient air at least partly to operate.

12. The device according to claim 11, wherein the pressure transducer includes a gauge pressure sensor.

13. The device according to claim 11, wherein the pressure transducer is configured to measure the pressure gradient between the first chamber and the second chamber.

14. The device according to claim 1, further comprising: a processing device configured to detect an underpressure or overpressure in the first chamber and/or the third chamber.

15. A delivery medical device comprising:
a movable wall and a rigid wall arranged into a hard housing having a bottom hard shell and a top hard shell;
a first chamber, a second chamber intended to store a fluid to be delivered to a patient, and a third chamber, the second chamber and the third chamber are tightly separated by the movable wall and at least one of the first chamber and the third chamber are configured to be watertight;
a fluid pathway configured to provide a fluid communication between the second chamber and the patient;
a pumping device configured to convey the fluid through the fluid pathway to the patient;
a vent device configured to vent at least one of the first chamber and the third chamber to the external environment of the delivery medical device;
a pressure transducer configured to measure the fluid pressure in the fluid pathway; and
an energy source for the pumping device located in the first chamber.

16. The device according to claim 15, wherein the energy source requires communication with ambient air.

17. The device according to claim 15, wherein the vent device is configured to vent at least one of the first chamber and the third chamber to provide a fluidic communication or a pressure equilibration between the first chamber and the air ambient or between the third chamber and the air ambient.

18. The device according to claim 15, wherein the vent device includes a first vent configured to vent the first chamber to the external environment of the delivery medical device.

19. The device according to claim 18, wherein the first vent includes a hydrophobic vent.

20. The device according to claim 15, wherein the vent device includes a second vent configured to vent the third chamber to the external environment of the delivery medical device.

21. The device according to claim 20, wherein the second vent provides an air communication and a liquid communication between the external environment and the third chamber.

22. The device according to claim 15, wherein the vent device includes a passage which extends toward inside the delivery medical device up to a baffle.

23. The device according to claim 22, wherein the baffle includes two opposite holes.

24. The device according to claim 22, wherein the baffle provides a mechanical protection against a tip object from the external environment.

25. The device according to claim 15, wherein the pressure transducer includes a gauge pressure sensor.

26. The device according to claim 15, wherein the pressure transducer is configured to measure the pressure gradient between the first chamber and the second chamber.

27. The device according to claim 15, further comprising:
a processing device configured to detect an underpressure or overpressure in the first chamber and/or the third chamber.

28. A delivery medical device comprising:
a movable membrane and a rigid wall arranged into a hard housing having a bottom hard shell and a top hard shell;
a first chamber, a second chamber intended to store a fluid to be delivered to a patient, and a third chamber defined by at least the flexible membrane and the rigid wall, the second chamber and the third chamber are tightly separated by the movable membrane and at least one of the first chamber and the third chamber have a watertight interface;
a fluid pathway configured to provide a fluid communication between the second chamber and the patient;
a pumping device configured to convey the fluid through the fluid pathway to the patient;
at least one unit, located in the first chamber, requiring communication with ambient air, the at least one unit requiring communication with the ambient air including at least one of an energy source and a pressure transducer; and
a vent device configured to vent at least one of the first chamber and the third chamber to provide a fluidic communication or a pressure equilibration between the first chamber and the air ambient or between the third chamber and the air ambient.

29. The device according to claim 28, wherein the vent device includes a first vent configured to vent the first chamber to the external environment of the delivery medical device.

30. The device according to claim 29, wherein the first vent includes a hydrophobic vent.

31. The device according to claim 28, wherein the vent device includes a second vent configured to vent the third chamber to the external environment of the delivery medical device.

32. The device according to claim 31, wherein the second vent provides an air communication and a liquid communication between the external environment and the third chamber.

33. The device according to claim 28, wherein the vent device includes a passage which extends toward inside the delivery medical device up to a baffle.

34. The device according to claim 33, wherein the baffle includes two opposite holes.

35. The device according to claim 33, wherein the baffle is configured to provide a mechanical protection against a tip object from the external environment.

36. The device according to claim 28, wherein the pressure transducer includes a gauge pressure sensor.

37. The device according to claim 28, wherein the pressure transducer is configured to measure the pressure gradient between the first chamber and the second chamber.

38. The device according to claim 28, further comprising:
a processing device configured to detect an underpressure or overpressure in the first chamber and/or the third chamber.

\* \* \* \* \*